United States Patent
Shelton et al.

(10) Patent No.: US 12,161,289 B2
(45) Date of Patent: Dec. 10, 2024

(54) AUTOMATIC IRRIGATION-COORDINATED LITHOTRIPSY

(71) Applicant: GYRUS ACMI, INC., Westborough, MA (US)

(72) Inventors: Kurt G. Shelton, Bedford, MA (US); Tailin Fan, Nashua, NH (US)

(73) Assignee: Gyrus ACMI, Inc., Westborough, MA (US)

(*) Notice: Subject to any disclaimer, the term of this patent is extended or adjusted under 35 U.S.C. 154(b) by 647 days.

(21) Appl. No.: 17/305,739

(22) Filed: Jul. 14, 2021

(65) Prior Publication Data

US 2021/0361356 A1    Nov. 25, 2021

Related U.S. Application Data

(63) Continuation of application No. 15/686,465, filed on Aug. 25, 2017, now Pat. No. 11,547,479.
(Continued)

(51) Int. Cl.
*A61B 1/00* (2006.01)
*A61B 1/015* (2006.01)
(Continued)

(52) U.S. Cl.
CPC .... *A61B 1/000095* (2022.02); *A61B 1/00009* (2013.01); *A61B 1/015* (2013.01);
(Continued)

(58) Field of Classification Search
CPC .............. A61B 1/307; A61B 17/22012; A61B 17/2202; A61B 18/26; A61B 90/37; A61B 2017/00022; A61B 2017/00039; A61B 2017/00088; A61B 2017/00092; A61B 2017/00123; A61B 2017/00181; A61B 2017/00185; A61B 2017/0019; A61B 2018/00511; A61B 2018/00642;
(Continued)

(56) References Cited

U.S. PATENT DOCUMENTS 9,956,040 B1    5/2018   Lastarria
11,547,479 B2*  1/2023   Shelton ............... A61M 3/0202
(Continued)

OTHER PUBLICATIONS

"U.S. Appl. No. 15/686,465, Advisory Action mailed Feb. 23, 2021", 3 pgs.
(Continued)

*Primary Examiner* — Michael J Lau
(74) *Attorney, Agent, or Firm* — Schwegman Lundberg & Woessner, P.A.

(57) ABSTRACT

Systems and methods for controlling an energy output setting of a lithotripsy device during a lithotripsy procedure are provided. The system includes a laser or other lithotripsy device configured for facilitating the lithotripsy procedure, an irrigation system configured for supplying an irrigant such as saline to a surgical site, and a temperature sensor configured to provide temperature data associated with the irrigant. The system can modulate the energy output setting of the lithotripsy device based on an estimated temperature that is determined based at least in part on the temperature data and one or more other factors such as a current energy output setting or a flow rate of the irrigant.

20 Claims, 4 Drawing Sheets

Related U.S. Application Data

(60) Provisional application No. 62/379,292, filed on Aug. 25, 2016.

(51) Int. Cl.
    *A61B 17/22*     (2006.01)
    *A61B 18/26*     (2006.01)
    *A61M 3/02*      (2006.01)
    A61B 1/307       (2006.01)
    A61B 17/00       (2006.01)
    A61B 18/00       (2006.01)
    A61B 90/00       (2016.01)

(52) U.S. Cl.
    CPC .... *A61B 17/22012* (2013.01); *A61B 17/2202* (2013.01); *A61B 18/26* (2013.01); *A61M 3/0202* (2021.05); *A61M 3/0254* (2013.01); A61B 1/307 (2013.01); A61B 2017/00022 (2013.01); A61B 2017/00039 (2013.01); A61B 2017/00088 (2013.01); A61B 2017/00092 (2013.01); A61B 2017/00123 (2013.01); A61B 2017/00181 (2013.01); A61B 2017/00185 (2013.01); A61B 2017/0019 (2013.01); A61B 2018/00511 (2013.01); A61B 2018/00642 (2013.01); A61B 2018/00744 (2013.01); A61B 2018/00815 (2013.01); A61B 2018/00821 (2013.01); A61B 90/37 (2016.02); A61B 2217/007 (2013.01); A61B 2218/002 (2013.01); A61M 3/0262 (2013.01); A61M 2205/3334 (2013.01); A61M 2210/1082 (2013.01); A61M 2230/005 (2013.01); A61M 2230/50 (2013.01)

(58) Field of Classification Search
    CPC ........... A61B 2018/00744; A61B 2018/00815; A61B 2018/00821; A61B 2217/007; A61B 2218/002; A61M 3/0202; A61M 3/0254; A61M 3/0262; A61M 2205/3334; A61M 2210/1082; A61M 2230/005; A61M 2230/50
    USPC ......................................................... 606/2.5
    See application file for complete search history.

(56) References Cited

U.S. PATENT DOCUMENTS

| | | | |
|---|---|---|---|
| 2005/0228425 A1 | 10/2005 | Boukhny et al. | |
| 2007/0083195 A1* | 4/2007 | Werneth | A61B 18/1492 606/41 |
| 2011/0125150 A1* | 5/2011 | Deno | A61B 5/6844 606/34 |
| 2011/0144429 A1 | 6/2011 | Finkman et al. | |
| 2011/0224667 A1* | 9/2011 | Koblish | A61B 18/1492 606/41 |
| 2011/0270242 A1 | 11/2011 | Marion | |
| 2012/0065553 A1 | 3/2012 | Lebet | |
| 2012/0165809 A1* | 6/2012 | Christian | A61B 18/1492 606/41 |
| 2012/0165812 A1* | 6/2012 | Christian | A61B 18/1492 606/41 |
| 2013/0274835 A1* | 10/2013 | Nissila | A61N 5/0618 607/88 |
| 2014/0275762 A1 | 9/2014 | Irby, III | |
| 2015/0032102 A1* | 1/2015 | Govari | A61B 18/1492 606/41 |
| 2015/0119645 A1* | 4/2015 | Baldwin | A61B 17/3462 600/114 |
| 2015/0272674 A1 | 10/2015 | Xuan et al. | |
| 2016/0067519 A1* | 3/2016 | Tranberg | A61N 5/0601 607/89 |
| 2016/0166320 A1 | 6/2016 | Ciulla et al. | |
| 2016/0199127 A1* | 7/2016 | Prutchi | A61B 18/1492 606/41 |
| 2017/0181794 A1 | 6/2017 | Govari et al. | |
| 2017/0333614 A1 | 11/2017 | Gao et al. | |
| 2018/0055568 A1 | 3/2018 | Shelton et al. | |
| 2018/0147009 A1 | 5/2018 | Buttar et al. | |
| 2023/0081712 A1 | 3/2023 | Shelton et al. | |

OTHER PUBLICATIONS

"U.S. Appl. No. 15/686,465, Examiner Interview Summary mailed Jun. 21, 2021", 3 pgs.
"U.S. Appl. No. 15/686,465, Final Office Action mailed Dec. 1, 2020", 16 pgs.
"U.S. Appl. No. 15/686,465, Non Final Office Action mailed Mar. 17, 2021", 16 pgs.
"U.S. Appl. No. 15/686,465, Non Final Office Action mailed Jun. 1, 2020", 16 pgs.
"U.S. Appl. No. 15/686,465, Response filed Jan. 21, 2021 to Final Office Action mailed Dec. 1, 2020", 11 pgs.
"U.S. Appl. No. 15/686,465, Response filed Mar. 1, 2021 to Advisory Action mailed Feb. 23, 2021", 11 pgs.
"U.S. Appl. No. 15/686,465, Response filed Apr. 28, 2020 to Restriction Requirement mailed Mar. 20, 2020", 6 pgs.
"U.S. Appl. No. 15/686,465, Response filed Jun. 15, 2021 to Non Final Office Action mailed Mar. 17, 2021", 12 pgs.
"U.S. Appl. No. 15/686,465, Response filed Aug. 26, 2020 to Non Final Office Action mailed Jun. 1, 2020", 10 pgs.
"U.S. Appl. No. 15/686,465, Restriction Requirement mailed Mar. 20, 2020", 9 pgs.
"U.S. Appl. No. 15/686,465, Advisory Action mailed Nov. 16, 2021", 3 pgs.
"U.S. Appl. No. 15/686,465, Examiner Interview Summary mailed Nov. 8, 2021", 2 pgs.
"U.S. Appl. No. 15/686,465, Final Office Action mailed Sep. 1, 2021", 10 pgs.
"U.S. Appl. No. 15/686,465, Response filed Oct. 29, 2021 to Final Office Action mailed Sep. 1, 2021", 11 pgs.
"U.S. Appl. No. 15/686,465, Examiner Interview Summary mailed Mar. 21, 2022", 2 pgs.
"U.S. Appl. No. 15/686,465, Non Final Office Action mailed Jan. 21, 2022", 12 pgs.
"U.S. Appl. No. 15/686,465, Response filed Mar. 18, 2022 to Non Final Office Action mailed Jan. 21, 2022", 10 pgs.
"U.S. Appl. No. 15/686,465, Final Office Action mailed Jun. 21, 2022", 12 pgs.
"U.S. Appl. No. 15/686,465, Notice of Allowance mailed Sep. 21, 2022", 10 pgs.
"U.S. Appl. No. 15/686,465, Response filed Aug. 18, 2022 to Final Office Action mailed Jun. 21, 2022", 9 pgs.

* cited by examiner

AUTOMATIC IRRIGATION-COORDINATED LITHOTRIPSY

RELATED APPLICATIONS

The present application is a continuation of and claims the benefit of priority to U.S. patent application Ser. No. 15/686,465, filed Aug. 25, 2017, which claims the benefit of and priority to U.S. Provisional Patent Application No. 62/379,292, filed Aug. 25, 2016, the entire contents of each being hereby incorporated by reference.

TECHNICAL FIELD

The present disclosure relates to a medical device. More specifically, the present disclosure relates to a lithotripsy system for fragmenting stone in a patient's body.

BACKGROUND

The statements in this section merely provide background information related to the present disclosure and may or may not constitute prior art.

Lithotripsy is a common method for fragmenting stones, or calculi, in the urinary tract, kidneys, and/or bladder. Most lithotripsy devices use ultrasound, laser, shockwave, or pneumatic energy sources to fragment such stones. Traditionally, the lithotripter includes a shaft connected to an electrically controlled driver or a pneumatic actuator. The shaft is inserted into the patient's anatomy to a location near the stone, and a waveform is sent through the shaft to impact the stone with the shaft to create a jackhammer or drilling effect on the stone, thus fragmenting the stone into smaller elements to be removed. Fragments are then removed, for example, by irrigation or basket. Recently, laser energy is replacing the use of ultrasound in lithotripsy as the smaller diameter laser fibers, compared to large diameter of the shaft, are less invasive.

In lithotripsy, irrigation may be used to clear the field of view to support an efficient stone management procedure. However, too much irrigation can create a retropulsion effect on stone fragments which makes it harder to target them with lithotripters and therefore reduces procedural efficiency. Further, in laser lithotripsy, irrigation may be used to remove the fragments from a patient's body. Using current laser lithotripsy systems, the operator controls the irrigation by controlling an irrigation pump system. These systems require that the operator continuously modulate the irrigation flow rate to balance the procedural needs of clear field of view and low fragment retropulsion.

Accordingly, there exists a need for more effective, simpler, and automated laser lithotripsy system.

SUMMARY

According to certain embodiments, a method for controlling an irrigation flow rate during lithotripsy is provided. The method may include receiving feedback from a lithotripsy system and setting the irrigation flow rate based on the received feedback.

According to other embodiments, a system for controlling an irrigation flow rate during lithotripsy is provided. The system may include a lithotripsy system, a pump, and an irrigation controller configured to receive feedback from the lithotripsy system and set an irrigation flow rate of the pump based on the received feedback.

BRIEF DESCRIPTION OF THE DRAWINGS

The forgoing and other features and advantages provided by the present disclosure may be better understood by referring to the following description taken in conjunction with the accompanying drawings. The drawings are not necessarily to scale, emphasis instead generally being placed upon illustrating the principles of the technology.

DESCRIPTION OF EXEMPLARY EMBODIMENTS

Figure 1:
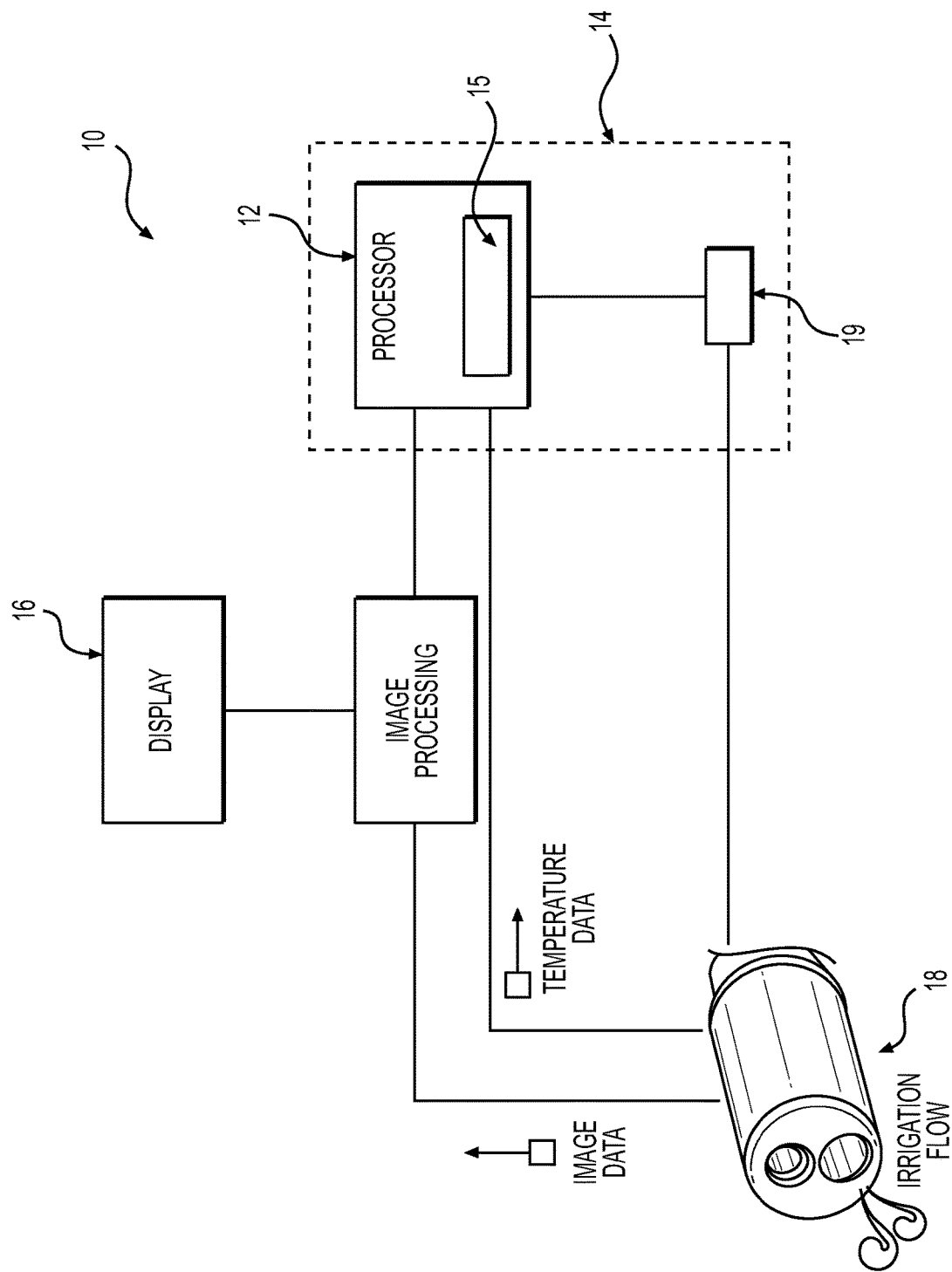
FIG. 1 illustrates a system for controlling an irrigation flow rate during lithotripsy according to certain embodiments.

Lithotripsy is a common method for fragmenting stones, or calculi, in the urinary tract, kidneys, and/or bladder. Working channels in rigid and flexible ureteroscopes carry accessories for performing lithotripsy of urinary calculi. These accessories include lithotripters such as ShockPulse® and LUS-2™ by Olympus Corporation of Tokyo, Japan, or Swiss Lithoclast® by Boston Scientific Corporation of Marlborough, Massachusetts, United States, and laser fibers for lithotripsy lasers. In addition to the accessories used to fragment calculi, the working channels also take part in the process of delivering irrigant, e.g., saline, to the site of the calculi. Irrigation may be required to clear the field of view to support an efficient stone management procedure. Irrigation could be implemented with an inflow and an outflow to manage intra-renal pressures. Too much irrigation flow can push calculi fragments out of the active lithotripsy field leading to longer procedures. Too much irrigation can also lead to renal hypothermia.

However, too little irrigation flow might not sufficiently clear the calculi fragments and dust from the field of view, leading to poor visibility and an inefficient lithotripsy procedure. Too little irrigation can also lead to thermal tissue damage in the collection system because many lithotripsy systems generate heat as they fragment calculi. Modern laser systems can deliver optical energy at significantly higher power levels while performing lithotripsy compared to traditional laser systems. Higher power lasers can break stones more quickly which can result in a cloudier field that requires higher irrigation flow rates to maintain a clear field of view. However, traditional laser lithotripsy systems do not include temperature sensing and/or automatic irrigation controlling elements. The majority of urolithiasis procedures are performed with irrigation flow system either provided by gravity feeding (e.g., hanging saline bag at a fixed height) or manually pushing a syringe to boost flow rate momentarily.

In flexible ureteroscopy procedures, a ureteroscope operator performs lithotripsy by viewing an image and the operator attempts to keep the field of view clear by controlling the irrigation pump system, e.g., an Irri-flow™ system by Olympus Corporation of Tokyo, Japan, a gravity feed system with modulation clamps, or a syringe pump system. These systems require that the operator continuously modulate the irrigation flow rate to meet the visibility needs without pushing fragments from the active lithotripsy field requiring the ureteroscope operator to chase them, reducing the efficiency of the procedure. As the rate of calculi fragment and dust formation through lithotripsy increases, visibility through an ureteroscope decreases unless an appropriate irrigation flow rate is maintained. The existing constant flow rate systems or syringe pumps are not well-suited for use with high efficiency lithotripsy systems, specifically, laser lithotripsy systems, due to their need for constant monitoring and adjustment, and for being a source of significant fatigue in the case of the hand-held syringe pump.

In rigid ureteroscopy procedures, due to larger working channels being available, irrigation systems are more capable to deliver higher irrigation flow rates, however the issues of fatigue and operator monitoring and adjustment are the same.

The current disclosure provides a system and method that automatically modulates the irrigation flow rate depending on feedback of the lithotripsy system. For example, in ultrasonic lithotripsy, the disclosed irrigation system may automatically increase irrigation flow when the transducer is energized, or when the lithotripsy system detects contact with a calculus or stone. In laser lithotripsy, the present irrigation system may automatically increase irrigation flow when the laser is being operated, or when the lithotripsy system detects contact with a stone or calculus. In contrast, the flow rate may be reduced when the ultrasonic transducer is not energized or the laser is not being operated. In addition, when the system does not detect contact with the stone, the irrigation flow rate may be reduced. The system of the present disclosure can be applied to any lithotripsy system.

The present disclosure can precisely and quickly adjust the irrigation flow rate. In one embodiment, the system can increase the flow precisely within an intrarenal pressure safety limit to clear the field of view quickly. The intrarenal pressure should not exceed a safety limit because excessive pressure in the kidney may be harmful to a patient (e.g., it may lead to pyelovenous backflow, a retrograde movement of fluid from renal pelvis into renal venous system).

In one embodiment, a method for controlling an irrigation flow rate during lithotripsy is provided. The method can include receiving feedback from a lithotripsy system and setting the irrigation flow rate based on the received feedback. The lithotripsy system can include a device for fragmenting stones. For example, a device using ultrasonic energy or a device using laser energy. The lithotripsy system can also include one or multiple screens to display an image of the area inside a patient's body where the stone or calculus is located or fragmentation of stone or calculus is happening. The lithotripsy system may include a processor to receive feedback and process the received feedback. The lithotripsy system may further include an irrigation system.

FIG. 1 illustrates a lithotripsy system 10, having a processor 12, lithotripsy irrigation system 14, a display 16, and a lithotripsy device 18. The irrigation system 10 further includes a pump 19. In one embodiment, the irrigation system measures fluid pressure at the pump output, which reflects the resistance, thus the pressure at the surgical site inside patient's body. Then, the system measures the flow delivered to the surgical site at pre-set value, based on the pressure feedback. The system tallies the effluent volume by weighting, thus monitoring the volume difference between inflow and outflow which is the missing fluid that stays inside patient's body, which can become hazardous if pressure exceeds. In one embodiment, the irrigation system is an open loop system. That is, the irrigation system controls the rate of fluid flowing into the patient's body. Therefore, the outflow would remain through the access sheath. The lithotripsy system of the present disclosure has further enhancement to the current flow management devices, in that the rate of inflow is automatically adjusted by the control section of the processor 12, based on the received feedback from the lithotripsy system 10. The processor may further include an irrigation controller 15 to control the irrigation flow rate, such as by an irrigation pump 19 of the irrigation system 14. That is, the processor can control the rate of irrigation inflow and outflow to and from the patient's body.

In one embodiment, the feedback can be an image processing data. The processor may include an image processing system to process the image data. In this embodiment, the image data can be processed in real time, monitoring the clarity of the image. This can be accomplished, for example, by looking for sharp edges or their absence, or transitions of grey level among image pixels in a region. Lack of sharp edges or bland view (i.e., low contrast) can indicate that the surgeon is also experiencing difficulties to discern the stone from debris cloud. Therefore, the image processing data indicates the image is blurry. When the blurriness exceeds a certain threshold, the processor can automatically command the irrigation system to increase the irrigation flow output of the irrigation pump 19 to remove the debris from field of view. Therefore, setting the irrigation flow rate can include increasing the irrigation flow rate if the image processing data indicated an image is blurry. When the field of view becomes clear enough according to the image processing data, the processor commands the irrigation controller 15 of the irrigation system 14 to decrease the irrigation flow rate or even stop the pump 19 temporarily. Therefore, setting the irrigation flow rate can include decreasing the irrigation flow rate if the image processing data indicates an image is clear. Reducing the flow rate may help stabilize the stone position.

Maintaining a clear field of view, keeping the stone stable to optimize the rate of stone fragmentation, and managing the temperature rise in the patient requires a lithotripsy surgeon/operator to find a balance between these often conflicting priorities. The present disclosure supports the surgeon/operator with this often task, and contributes to improving procedure efficiency and safety.

In addition to adjusting irrigation flow rate to clear the view, a surgeon also has the option of reducing the lithotripsy intensity to gain view clarity back. During laser lithotripsy, the laser energy is spent in breaking chemical bonds and creating new surfaces, which both lead to stone disintegration. A portion of the total energy is spent heating up the fluid inside the patient's body at the surgical space. In one embodiment, the lithotripsy system can include a temperature sensor configured to provide input to enable control of a flow of the lithotripsy irrigation system in response to a change in temperature from the operation of the laser. The temperature sensor can be any sensor to sense the temperature. For example, the temperature sensor can be a thermocouple, a thermistor, or any suitable temperature sensor.

By keeping track of the irrigation inflow and outflow volumes, the temperature of irrigation inflow and outflow, and the laser energy setting (e.g., joules per pulse), example embodiments of the present invention can monitor the amount of energy having gone into and out of the surgical space. Equation (1) demonstrates this relation.

$$t = t_{inflow} + 0.239 \Delta E / \Delta V \quad (1)$$

$\Delta E$ is energy accumulative difference (in joules) at the moment of time $\tau$, $\Delta V$ is the amount of irrigation fluid going into and out of the surgical space at the same time τ (in cubic centimeters), and t is the average temperature of the irrigation fluid at time t inside the surgical volume.

Equation (1), applied to the present system, can be used to estimate the temperature of the patient's surgical place by monitoring over the same time duration, the inflow and outflow irrigation volumes, the energy added to the patient by the lithotripter, and the temperature of the inflow fluid, e.g., saline.

Figure 2:
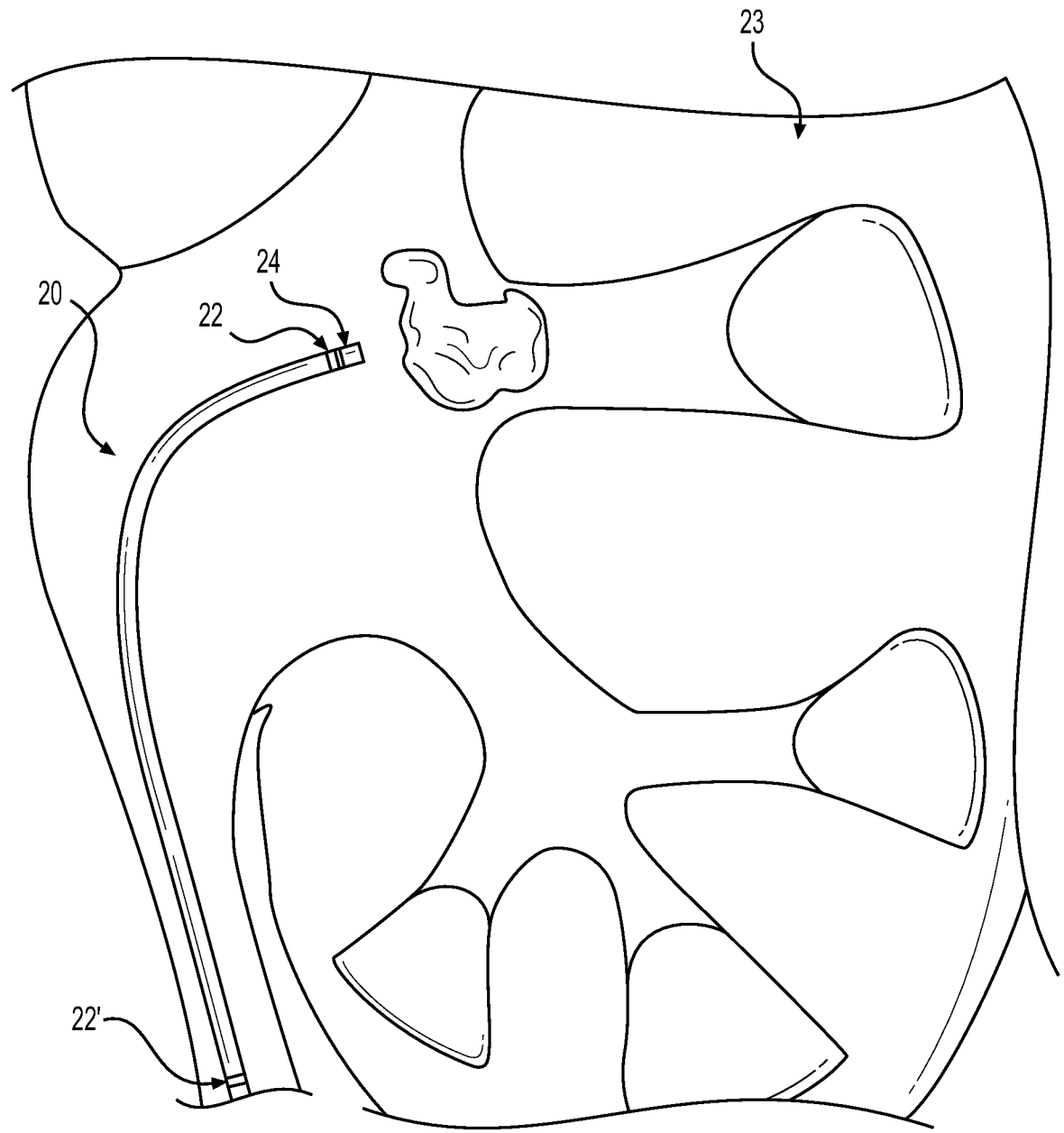
FIG. 2 illustrates a device for sensing temperature according to certain embodiments.

FIG. 2 illustrates temperature sensors 22, 22' at various part of the device, e.g., on the flexible tip 24 of endoscope 20 and on the endoscope 20 far from the tip of the endoscope. The temperature sensor can be located at various part of the device. In one embodiment the system can include an endoscope having a distal end and a proximal end. The temperature sensor can be located on the distal end of the endoscope which is inserted in the patient's body. The distal end of the endoscope 20 is located inside the patient's body 23.

Figure 3:
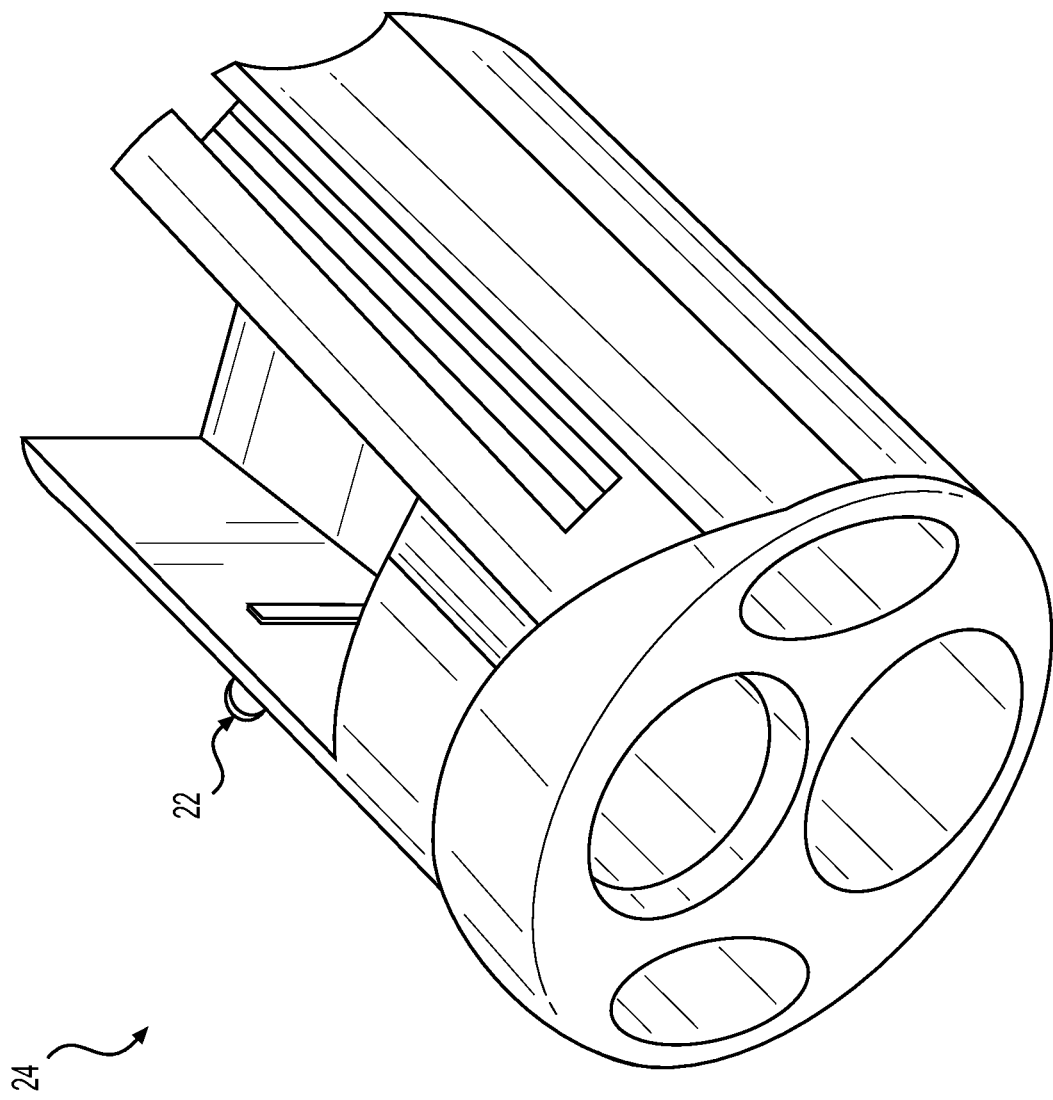
FIG. 3 illustrates a close view of a device for sensing temperature according to certain embodiments.

FIG. 3 illustrates a close view of a device which the temperature sensor 22 located on the tip of the endoscope 20 and on the outer surface of the endoscope 20. Although in FIG. 3, multiple temperature sensors are shown on endoscope 20, one ordinary skill in the art would acknowledge that one or even more temperature sensors can be located on the endoscope. In one embodiment, the temperature sensor can be located on the endoscope outside of the patient's body near the irrigation outflow path from the patient's body.

In one embodiment, the feedback can be irrigation fluid temperature data. Therefore, the system can increase the irrigation flow rate when receiving a feedback that the temperature is more than a predetermined value. As stated above, the processor of the system receives temperature feedback from the system and can determine if the temperature is higher than a predetermined value. The predetermined value of the temperature can be a temperature which does not harm the tissue of the surgical place. If the processor indicates that the received temperature feedback is higher than the predetermined value, it will increase the irrigation flow rate brining the temperature to the acceptable range or predetermined value. On the other hand, if the processor indicates that the received temperature feedback is lower than the predetermined value and the laser is not being operated, it can decrease the irrigation flow rate brining the feedback temperature to the acceptable range or the predetermined value.

In one embodiment, the processor receives feedback from the lithotripsy system and can control the energy output of the lithotripsy device. In one embodiment, the processor receives temperature feedback. If the processor receives temperature feedback and indicates that the temperature at the surgical place of the patient is more than predetermined value, the processor controls the energy of the lithotripter, i.e., reducing the energy or even stopping the operation of the lithotripter. In one embodiment, the processor receives feedback which is an image processing data. If the image processing data indicates that the image is blurry, the processor can control the energy of the lithotripter, i.e., reducing the energy or even stopping the operation of the lithotripter to clear the field of view.

Figure 4:
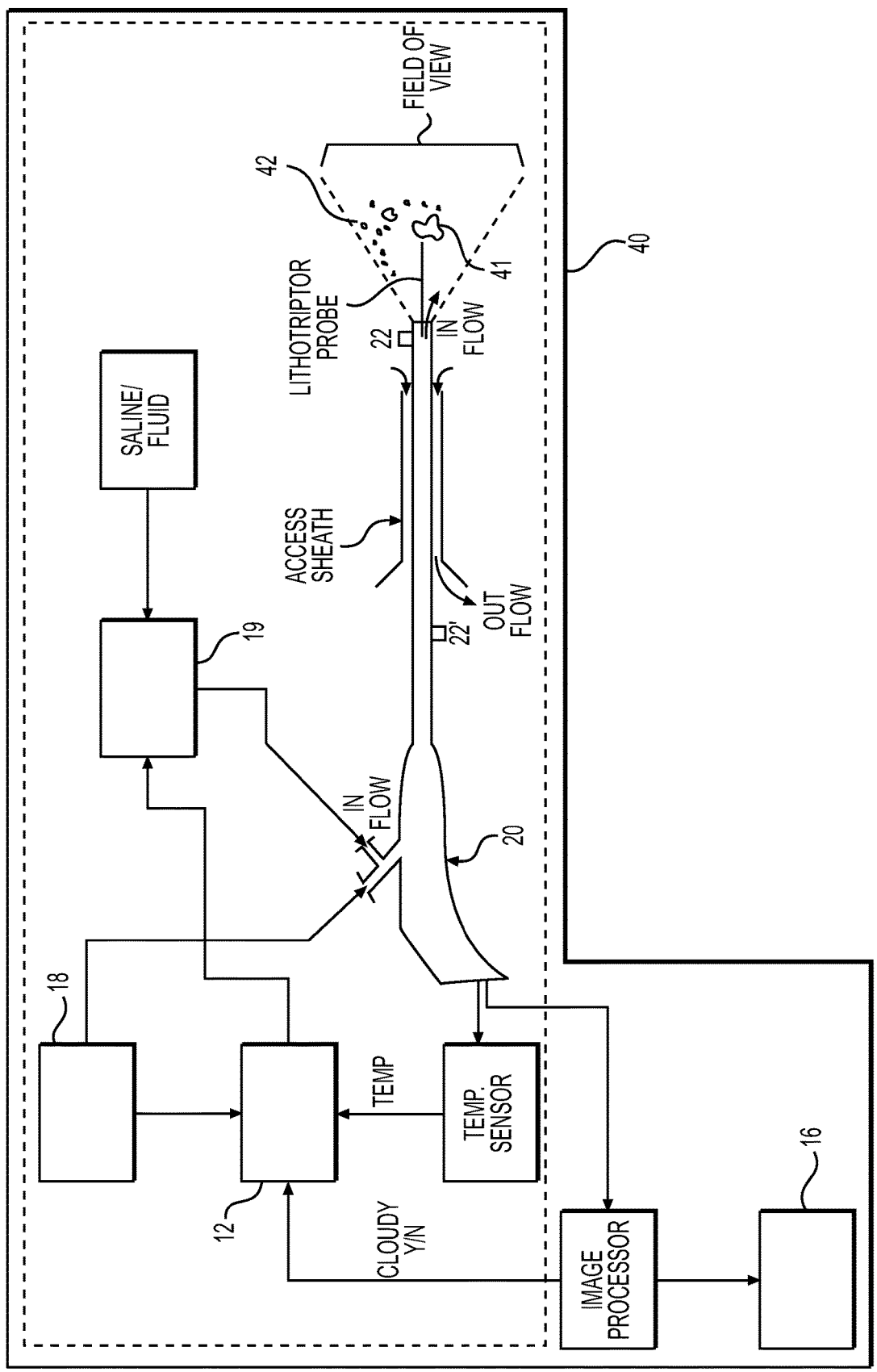
FIG. 4 illustrates a system for controlling an irrigation flow rate during lithotripsy according to certain embodiments.

FIG. 4 illustrates a lithotripsy system according to one embodiment of the present disclosure. The lithotripsy system 40 includes an endoscope 20. The endoscope having a channel for inflow of the irrigation flow and a channel for lithotripsy device 18. Fluid, e.g., saline can be introduced to patient's body through pump 19. The lithotripter probe of the lithotripsy device 18 targets the stone 41 to break it into fragments 42. The processor 12 receives feedback from the lithotripsy system 40. The feedback can be temperature data or image processing data. If the feedback is image processing data and indicates that the image is blurry, the processor can increase the irrigation flow rate through pump 19 to clear the field of view. In certain embodiments, if the irrigation flow rates reach a predetermined value, the processor can control the energy of the lithotripsy device 18. The processor can then stop the operation of the lithotripsy device 18 or adjust the energy of the lithotripsy device 18 to clear the field of view. If the feedback is temperature data and the processor can analyze the data and can indicate if the temperature has high or has reached a predetermined value. If the processor indicates that the temperature of the surgical place in the patient's body is high, it can increase the irrigation flow rate to bring the temperature in the acceptable range to prevent or reduce the tissue damage. In one embodiment, the processor can control the energy of the lithotripsy device 18. The processor can then stop the operation of the lithotripsy device 18 or adjust the energy of the lithotripsy device 18 to bring the temperature of the surgical place inside the patient's body to a predetermined value or lower than the predetermined value.

In one embodiment, the processor can change the nature of energy delivery to the stone to reduce the rate of fragment generation, e.g., by reducing the frequency, peak pulse power, and/or increasing the energy per pulse in a laser lithotripter system.

In one embodiment, the lithotripsy system may include a pressure sensor. The pressure sensor can be any suitable pressure sensor. The pressure sensor can be located at various part of the device. In one embodiment, the pressure sensor is located on the distal end of the endoscope located inside the patient's body to measure the pressure of the surgical place.

In one exemplary embodiment, the lithotripsy system controls the fluid inflow rate to higher, lower, or medium rates based on one or more feedbacks. These feedbacks can include if the lithotripter is currently ON or OFF, if the field of view is blurry or clear based on the image processing data, and a temperature feedback indicating of high, medium, or low. For example, a low temperature can be in the range of 10 to 35 degrees centigrade, a medium temperature can be in the range of 30 to 45 degrees centigrade, and a high temperature can be in the range above 40 degrees centigrade. A low inflow rate can be between 0 and 60 ml/min, a medium inflow rate can be between 50 and 160 ml/min, and a high inflow rate can be between 150 ml/min and 300 ml/min. Higher inflow rates such as up to 500 ml/min may be applied in short bursts in particular situations such as in the bladder or to flush difficult to access fragments from calyces.

In the above exemplary embodiment, the processor can set a low irrigation flow rate when the temperature in the surgical place of the patient is calculated or measured to be low, and the image is clear. The processor can set a medium flow rate when the temperature is either low or medium and the image is cloudy for less than between 3 and 20 seconds. If the image in this situation is cloudy for more than between 3 and 20 seconds, then the processor can set a high flow rate until the image becomes clear. Whenever the lithotripter is OFF and the image is cloudy or the temperature is at least medium, the processor can set a high flow rate. Whenever the temperature is high, the flow rate can be set to a high level.

What is claimed is:

1. A method for controlling an energy output setting of a lithotripsy device during a lithotripsy procedure, the method comprising:
    receiving, from a temperature sensor positioned at a first location, temperature feedback data that indicates a temperature of an irrigation fluid during the lithotripsy procedure;
    determining an estimated temperature at a second location based on (i) the temperature feedback data and (ii) an amount of energy emitted from the lithotripsy device per unit net volume of the irrigation fluid; and
    modulating, during the lithotripsy procedure, the energy output setting based on the estimated temperature at the second location.

2. The method of claim 1, wherein the first location is outside of a body of a patient during the lithotripsy procedure and the second location is inside of the body of the patient during the lithotripsy procedure.

3. The method of claim 1, wherein the temperature sensor is disposed at an irrigation outflow located outside of a body of a patient during the lithotripsy procedure.

4. The method of claim 1, wherein the temperature sensor is disposed at an irrigation inflow located outside of a body of a patient during the lithotripsy procedure.

5. The method of claim 1, wherein the determining the estimated temperature at the second location is further based on a flow rate of the irrigation fluid sensed using a flow sensor.

6. The method of claim 1, wherein the modulating the energy output setting includes stopping operation of the lithotripsy device during the lithotripsy procedure in response to the estimated temperature at the second location reaching a predetermined value.

7. The method of claim 1, wherein the modulating the energy output setting includes reducing the energy output setting to reduce the estimated temperature at the second location.

8. The method of claim 1, further comprising modulating, during the lithotripsy procedure, a flow rate of the irrigation fluid based on the estimated temperature at the second location.

9. The method of claim 1, wherein the determining the estimated temperature at the second location includes:
    determining the amount of energy per unit net volume of the irrigation fluid, including determining a ratio of a net energy emitted from the lithotripsy device to a net volume of irrigation fluid supplied to the first location;
    determining a first value representing the determined ratio scaled by a predetermined constant value; and
    combining the first value with the temperature of the irrigation fluid indicated by the temperature feedback data that is received from the temperature sensor positioned at the first location.

10. The method of claim 1, wherein the amount of energy emitted from the lithotripsy device is based on an accumulative energy of a plurality of pulses of the lithotripsy device.

11. The method of claim 1, the lithotripsy device includes a laser.

12. A system comprising:
    a lithotripsy device configured to emit energy at a first location inside a body of a patient;
    a temperature sensor configured to generate temperature feedback data that indicates a temperature of an irrigation fluid being supplied to the first location; and
    a controller configured to:
        determine an amount of energy emitted by the lithotripsy device within a particular duration of time per unit net volume of the irrigation fluid;
        determining an estimated temperature at a second location different from the first location based at least in part on (i) the temperature feedback data and (ii) the amount of energy emitted from the lithotripsy device per unit net volume of the irrigation fluid; and
        modulate an energy output setting of the lithotripsy device during a lithotripsy procedure based on the estimated temperature at the second location and the temperature feedback data.

13. The system of claim 12, wherein the controller is further configured to modulate the energy output setting of the lithotripsy device during the lithotripsy procedure based on flow rate information of the irrigation fluid.

14. The system of claim 12, wherein the controller is further configured to determine the amount of the energy based on a plurality of individual amounts of energy corresponding to a plurality of individual pulses of the lithotripsy device.

15. The system of claim 12, wherein the second location is an irrigation outflow located outside the body of the patient.

16. The system of claim 12, wherein to modulate the energy output setting includes to stop operation of the lithotripsy device during the lithotripsy procedure in response to the estimated temperature at the first location reaching a predetermined value.

17. The system of claim 12, wherein to modulate the energy output setting includes to reduce the energy output setting to reduce the estimated temperature at the first location.

18. A system comprising:
    a lithotripsy device;
    a temperature sensor configured to generate temperature feedback data that indicates a temperature of an irrigation fluid;
    a flow sensor configured to generate flow rate data that indicates a flow rate of the irrigation fluid; and
    a controller configured to:
        determine an amount of energy emitted by the lithotripsy device within a body of a patient within a particular duration of time per unit net volume of the irrigation fluid;
        modulate an energy output setting of the lithotripsy device during a lithotripsy procedure based on the temperature feedback data, the flow rate data, and the amount of energy emitted from the lithotripsy device per unit net volume of the irrigation fluid; and
        generate a control signal to the lithotripsy device to cause emission of energy in accordance with the modulated energy output setting.

19. The system of claim 18, wherein the controller is further configured to:
    determine an estimated temperature within the body of the patient based on the temperature feedback data, the flow rate data, and the amount of energy emitted per unit net volume of the irrigation fluid; and
    modulate the energy output setting based on the estimated temperature.

20. The system of claim 18, wherein the temperature feedback data indicates the temperature of the irrigation fluid at an irrigation inlet that is outside of the body of the patient.

* * * * *